United States Patent [19]

Wedemeyer et al.

[11] 4,324,913
[45] Apr. 13, 1982

[54] PROCESS FOR THE PREPARATION OF 4-NITROSO-DIPHENYL-AMINE

[75] Inventors: Karlfried Wedemeyer, Cologne; Lutz Kienitz, Bergisch-Gladbach, both of Fed. Rep. of Germany

[73] Assignee: Bayer Aktiengesellschaft, Leverkusen, Fed. Rep. of Germany

[21] Appl. No.: 183,202

[22] Filed: Sep. 2, 1980

[30] Foreign Application Priority Data

Sep. 5, 1979 [DE] Fed. Rep. of Germany ....... 2935775

[51] Int. Cl.³ .................... C07C 85/145; C07C 85/00
[52] U.S. Cl. .................................... 564/410; 564/441
[58] Field of Search ................................ 564/410, 441

[56] References Cited

U.S. PATENT DOCUMENTS

| 2,782,235 | 2/1957 | Lantz et al. | 564/410 |
| 4,034,042 | 7/1977 | Wedemeyer et al. | 564/410 |
| 4,102,926 | 7/1978 | Usvyatsov et al. | 564/410 |

FOREIGN PATENT DOCUMENTS

| 2654936 | 8/1978 | Fed. Rep. of Germany | 564/410 |
| 773236 | 4/1957 | United Kingdom | 564/410 |

Primary Examiner—John Doll
Attorney, Agent, or Firm—Connolly and Hutz

[57] ABSTRACT

A process for the preparation of 4-nitroso-diphenylamine by rearranging N-nitroso-diphenylamine according to Fischer-Hepp to o-dichlorobenzene, under the effect of alcoholic hydrochloric acid and working up the suspension of the 4-nitroso-diphenylamine-hydrochloride.

7 Claims, No Drawings

PROCESS FOR THE PREPARATION OF 4-NITROSO-DIPHENYL-AMINE

The present invention relates to a process for the preparation of 4-nitroso-diphenylamine by rearranging N-nitroso-diphenylamine according to Fischer-Hepp in an inert solvent which is immiscible with water, under the effect of alcoholic hydrochloric acid and by working up the suspension of 4-nitroso-diphenylamine-hydrochloride, with aqueous alkalis.

4-Nitroso-diphenylamine is an important intermediate for the protection of age-resistors for rubber, or dyes or compositions for protection against corrosion.

The preparation is carried out almost without exception by the N-nitrosation of diphenylamine and by rearranging the resulting N-nitroso-diphenylamine according to Fischer-Hepp. A whole series of variations has been described for this rearrangement reaction. The N-nitroso-compound is generally introduced into an inert, water-immiscible solvent and is rearranged under the effect of methanolic or alcoholic hydrochloric acid. A suspension of 4-nitroso-diphenylamine-hydrochloride is initially produced. Since 4-nitroso-diphenylamine is an acid in its tautomeric form, p-benzoquinone-aniloxime, it may be extracted in the form of its alkali salt using an aqueous alkali. Thus, a separation is obtained of non-rearranged N-nitroso-diphenylamine, of diphenylamine as the denitrosation product and of other decomposition products which remain in the organic phase since they are alkali-insoluble. By neutralising, using diluted mineral salts, the free 4-nitroso-diphenylamine may be obtained. The aqueous-alkaline solution may however also be used directly for reduction to 4-amino-diphenylamine.

U.S. Pat. Nos. 3,748,362 and 3,728,392 or German Offenlegungsschrift No. 2,654,936 are mentioned as examples of this working method. The water-immiscible solvents used in these Examples have certain advantages. Aromatic hydrocarbons such as benzene and toluene, among others, as a solvent for N-nitroso-diphenylamine lead to coarse-grained, easily sedimenting suspensions of 4-nitroso-diphenylamine-hydrochloride, as a result of their low density. The particles of these suspensions also tend to bake. Such suspensions can only be pumped with difficulty so that a disturbance-free, continuous working method in multi-stage cascades is not afforded. Thus, the continuous rearrangement only in trichloro ethylene is described in German Offenlegungsschrift No. 2,654,936. In German Offenlegungsschrift No. 2,211,341, the difficulty in dealing with 4-nitroso-diphenylamine-hydrochloride-suspensions is met by providing for a complete solution by use of a correspondingly increased quantity of solvent. However, this working method is associated with high expenditure in quantities of hydrogen chloride, which leads to an increased salt yield in the subsequent neutralisation step.

If the process is carried out using methanol or other alcohols without an additional solvent (e.g. U.S. Pat. Nos. 2,046,356 or 3,429,924) then the recovery of the alcohol becomes problematic and any advantage of separating the non-rearranged N-nitroso-diphenylamine and the decomposition products is lost.

Using chlorobenzene as a co-solvent for N-nitroso-diphenylamine has the disadvantage that, as a result of the unfavourable density ratios, the separation between the organic and the aqueous-alkaline phase is wearisome. Trichloroethylene would be per se the selected solvent. Both in a continuous as well as in a discontinuous working method, high yields are obtained, the initially produced 4-nitroso-diphenylamine-hydrochloride-suspension is fine-grained and may be pumped (German Offenlegungsschrift No. 2,654,936; N. V. Martynov, L. V. Muratova, V. F. Pivovarova, Khim. Prom.-st' 1976, (9), 657–9). However, as trichloroethylene has been found to be carcinogenic in experiments with animals, (sec Registry of Toxic Effects of Chemical Substances, NIOSH Vol. II, (1977) it is necessary to replace trichloroethylene with another solvent having the advantages of trichloroethylene but without its toxicological reservations.

A process has now been found to rearrange N-nitroso-diphenylamine into 4-nitroso-diphenylamine according to Fischer-Hepp, in an inert, water-immiscible solvent under the effect of alcoholic hydrochloric acid and working up the 4-nitroso-diphenylamine-hydrochloride-suspension, by extraction using aqueous alkalis, in which process o-dichlorobenzene is used as the water-immiscible solvent.

It is possible to use any sequence of addition for the starting materials. It is feasible to add the organic solution of the N-nitroso product to the alcoholic hydrochloric acid solution, and also vice versa.

In the process of the invention, it is preferable to introduce the N-nitroso-diphenylamine into o-dichlorobenzene. The concentration ratios are thereby not critical. The lower limit is governed by expediency considerations and the upper limit is governed by the solubility of the N-nitroso-diphenylamine. To dilute solutions lead to an unfavourable space-time yield. From 5 to 50% by weight solutions are preferred.

The acidic catalyst required for the rearrangement is used in the form of an alcoholic hydrochloric acid. As alcohols, alkanols of the type $C_nH_{2n+1}OH$ (where n = from 1 to 6) or cycloalkanols of the type $C_{n_1}H_{2n_1-1}OH$ where ($n_1 = 5$ or 6), are suitable. If alkanols which are miscible with water are used, then those are appropriately selected which have boiling points lower than that of water, so that an easy recovery from the aqueous phase is provided. Methanol, ethanol or isopropanol are preferably used, methanol being particularly preferred. The quantity of the acidic catalyst required for rearrangement is at least 100 mol % based on the N-nitroso-diphenylamine used, and the upper limit is governed only by the economy of the process. From 100 to 500 mol % are preferred. The alcoholic hydrochloric acid used as the acidic catalyst is used in the form of 5% by weight to saturated solutions in the alcohols mentioned above. The reaction temperatures may be between 0° and 50°, whereby an upper limit is imposed by the instability of the 4-nitroso-diphenylamine-hydrochloride. The reaction time is selected between 1 and 10 hours, whereby a prolongation is again a disadvantage as a result of the instability of the 4-nitroso-diphenylamine-hydrochloride. Since the 4-nitroso-diphenylamine is an acid in its tautomeric form-p-benzoquinone-aniloxime, it may also be extracted from the reaction mixture obtained after rearrangement using aqueous alkalis. Soda lye, potash lye and soda solution may be used as the aqueous alkalis. Soda lye is preferably used. The concentration is not critical and may be from 5 to 50% by weight. The quantity of alkali must at least suffice to neutralise the acidic catalysts used for rearrangement and to convert the 4-nitroso-diphenylamine into its alkali salt and preferably amounts to from 200 to 1000 mol %, based on the used quantity of the N-nitroso-diphenylamine. The aqueous-alkaline extract is separated and may be used directly in the reduction to 4-amino-diphenylamine. However, from the aqueous-alkaline extract, the free 4-nitroso-diphenylamine may also be released by neutralisation using dilute mineral salts.

The process according to the invention allows the preparation of 4-nitroso-diphenylamine in high yields and in excellent purity. The present process particularly avoids using trichloroethylene which is preferred in the known variations, but which is recognised as being carcinogenic in animal experiments.

The use of o-dichlorobenzene produces distinguished results with a discontinuous working method but also particularly allows a discontinuous working method in multi-stage cascades, as the suspension of the initially produced 4-nitroso-diphenylamine-hydrochloride in o-dichlorobenzen can be just as effectively pumped as the suspension in trichloroethylene. It is also unnecessary to use the N-nitroso-diphenylamine in isolated form. On the contrary, it is possible to carry out the N-nitrosation of the diphenylamine in the two-phase system aqueous sulphuric acid/o-dichlorobenzene, and directly to use the resulting solution of N-nitroso-diphenylamine in the organic phase in the rearrangement reaction. The process according to the invention already allows the rearrangement using low expenditure in quantities of hydrogen chloride so that the salt yield is low when working up.

The process is illustrated by the following Examples.

EXAMPLE 1

A 20% by weight solution of 99 g (0.5 M) N-nitroso-diphenylamine in o-dichlorobenzene is introduced into a flask fitted with a stirrer, a dropping funnel, an internal thermometer and a reflux condenser, and 25.6 g (0.7 M) of hydrogen chloride (corresponding to 140 mol % based on the N-nitroso-diphenylamine) in the form of a 35% by weight methanolic hydrochloric acid are introduced dropwise at 20° C. for 0.5 hours. This is then stirred for 8 hours, the reaction mixture is added to a solution of 80 g of NaOH in 720 ml of water, which this is then stirred for 0.5 hour. The organic phase is separated and is extracted using 200 ml of 10% by weight soda lye. 94 g ≙ 95% of 4-nitroso-diphenylamine having a melting point of 145°–147° is obtained from the combined aqueous-alkaline extracts, by neutralisation using 20% by weight sulphuric acid. The organic phase still contains 0.4 g ≙ 0.4% of 4-nitroso-diphenylamine, 2.7 g ≙ 2.7% of non-rearranged N-nitroso-diphenylamine and 1.2 g ≙ 1.4% of diphenylamine (denitrosation product). Thereby, the yield based on the conversion of the N-nitroso-diphenylamine amount to 97.6%.

The analysis is carried out using high pressure liquid chromatography against o-terphenyl as the internal standard, for the control, the 4-nitroso-diphenylamine is titrated potentiometrically using tetrabutyl ammonium hydroxide in isopropanol.

EXAMPLE 2

A 22% by weight solution of N-nitroso-diphenylamine in o-dichlorobenzene and a 35% by weight methanolic hydrochloric acid are simultaneously pumped into a cascade consisting of 4 double-walled, separately cooled stirring vessels which are connected in tandem such that the molar ratio of HCl to N-nitroso-diphenylamine is 1.4 and the residence time per vessel is 3.11 hours. The temperature is maintained at 20° C. The reaction mixture is passed from the last vessel into a collecting vessel which is filled with excess 10% by weight soda lye. The organic phase is separated and extracted using 10% by weight soda lye and the combined aqueous-alkaline solutions are neutralised using 20%-sulphuric acid. A 4-nitroso-diphenylamine is obtained having a melting point of 146°–147°, the yield is 93%. Approximately 5% of unconverted N-nitroso-diphenylamine are still contained in the organic phase.

We claim:

1. In the process of preparing 4-nitroso-diphenylamine by the steps of rearraning N-nitroso-diphenylamine according to Fischer-Hepp in an inert solvent which is immiscible with water under the effect of alcoholic hydrochloric acid and working up the suspension of thusly produced 4-nitroso-diphenylamine-hydrochloride by extraction with aqueous alkali, the improvement wherein o-dichlorobenzene is used as the water-immiscible solvent.

2. The process of claim 1 wherein the N-nitroso-diphenylamine is used as a 5% by weight solution to a saturated solution.

3. The process of claim 1 wherein the N-nitroso-diphenylamine is used in the form of a 5 to 50% by weight solution.

4. The process of claim 1 wherein the alcoholic hydrochloric acid is used as a 5% by weight solution to a saturated solution.

5. The process of claim 1 wherein the alcoholic hydrochloric acid is used in a quantity of from 100 to 500 mol % based on the N-nitroso-diphenylamine.

6. The process of claim 1 wherein the alcohol of said alcoholic hydrochloric acid is an alkanol having from 1 to 6 carbon atoms or a cycloalkanol having from 5 to 6 carbon atoms.

7. The process of claim 1 wherein the alcohol of said alcoholic hydrochloric acid is at least one member selected from the group consisting of methanol, ethanol and isopropanol.

* * * * *